US011311269B2

(12) United States Patent
Dunbar et al.

(10) Patent No.: US 11,311,269 B2
(45) Date of Patent: Apr. 26, 2022

(54) ULTRASOUND IMAGING SYSTEM AND METHOD FOR PROVIDING ASSISTANCE IN AN ULTRASOUND IMAGING SYSTEM (71) Applicant: EZONO AG, Jena (DE)

(72) Inventors: Allan Dunbar, Jena (DE); Sicco Schets, Jena (DE); Fateh Mohammed, Jena (DE); Hiba Arbash, Jena (DE)

(73) Assignee: EZONO AG, Jena (DE)

( * ) Notice: Subject to any disclaimer, the term of this patent is extended or adjusted under 35 U.S.C. 154(b) by 165 days.

(21) Appl. No.: 16/242,803

(22) Filed: Jan. 8, 2019

(65) Prior Publication Data
US 2019/0142362 A1 May 16, 2019

Related U.S. Application Data (63) Continuation of application No. 12/988,730, filed as application No. PCT/EP2008/054832 on Apr. 22, 2008, now abandoned.

(51) Int. Cl.
A61B 8/00 (2006.01)
G09B 23/28 (2006.01)
G16H 40/63 (2018.01)
G16H 30/20 (2018.01)
G16H 30/40 (2018.01)

(52) U.S. Cl.
CPC ............... A61B 8/00 (2013.01); A61B 8/463 (2013.01); G09B 23/286 (2013.01); G16H 30/20 (2018.01); G16H 30/40 (2018.01); G16H 40/63 (2018.01)

(58) Field of Classification Search
None
See application file for complete search history.

(56) References Cited

U.S. PATENT DOCUMENTS

| 2,612,074 A | 9/1952 | Mirau et al. |
| 4,381,676 A | 5/1983 | Kaule et al. |
| 4,762,413 A | 8/1988 | Namba et al. |
| 5,146,079 A | 9/1992 | Lisco |
| 5,211,165 A | 5/1993 | Dumoulin et al. |
| 5,735,276 A | 4/1998 | Lemeison |
| 5,791,907 A | 8/1998 | Ramshaw et al. |

(Continued)

FOREIGN PATENT DOCUMENTS

| EP | 1156345 A2 | 11/2001 |
| EP | 1559373 A2 | 8/2005 |

(Continued)

OTHER PUBLICATIONS

English translation for JP 4135546 (Year: 1992).*

(Continued)

Primary Examiner — Katherine L Fernandez
(74) Attorney, Agent, or Firm — Birch, Stewart, Kolasch & Birch, LLP (57) ABSTRACT An ultrasound imaging system comprising an ultrasound scanner for acquiring a live ultrasound image of a portion of the anatomy of a patient being examined with the ultrasound imaging system, an assistance means for providing at least one primary demonstration video clip, and at least one video display. The video display is functionally connected with the ultrasound scanner and the assistance means in order to present the primary demonstration video clip simultaneously with a live ultrasound image.

18 Claims, 4 Drawing Sheets

(56) References Cited

U.S. PATENT DOCUMENTS

| | | | |
|---|---|---|---|
| 5,832,055 A | 11/1998 | Dewaele | |
| 6,390,978 B1 | 5/2002 | Irion et al. | |
| 6,436,049 B1 | 8/2002 | Kamiyama et al. | |
| 6,458,081 B1 * | 10/2002 | Matsui | A61B 8/467 |
| | | | 600/437 |
| 6,468,217 B1 * | 10/2002 | Fazioli | G06F 19/321 |
| | | | 600/443 |
| 6,488,629 B1 | 12/2002 | Saetre et al. | |
| 6,656,120 B2 | 12/2003 | Lee et al. | |
| 7,041,058 B2 | 5/2006 | Piehler | |
| 7,263,710 B1 | 8/2007 | Hummel, Jr. et al. | |
| 7,806,824 B2 * | 10/2010 | Ohtake | A61B 8/42 |
| | | | 600/443 |
| 2001/0010003 A1 | 7/2001 | Lai | |
| 2001/0039836 A1 | 11/2001 | Ogawa | |
| 2001/0042410 A1 | 11/2001 | Ogawa | |
| 2002/0087080 A1 | 7/2002 | Slayton et al. | |
| 2002/0156375 A1 | 10/2002 | Kessman et al. | |
| 2004/0019270 A1 * | 1/2004 | Takeuchi | A61B 8/0883 |
| | | | 600/407 |
| 2005/0036668 A1 | 2/2005 | McLennan et al. | |
| 2005/0068221 A1 | 3/2005 | Freeman et al. | |
| 2005/0090742 A1 * | 4/2005 | Mine | A61B 34/20 |
| | | | 600/443 |
| 2005/0096545 A1 | 5/2005 | Haider et al. | |
| 2007/0010743 A1 | 1/2007 | Arai | |
| 2007/0239001 A1 | 10/2007 | Mehi et al. | |
| 2008/0187896 A1 * | 8/2008 | Savitsky | G09B 23/288 |
| | | | 434/272 |
| 2008/0249402 A1 | 10/2008 | Szucs et al. | |
| 2009/0024030 A1 * | 1/2009 | Lachaine | A61B 8/4416 |
| | | | 600/437 |

FOREIGN PATENT DOCUMENTS

| | | | |
|---|---|---|---|
| JP | 4135546 | * | 5/1992 |
| JP | 4135546 A | | 5/1992 |
| WO | WO 2003/100363 A2 | | 12/2003 |
| WO | WO 2004/058072 A1 | | 7/2004 |
| WO | WO 2004/098414 A1 | | 11/2004 |
| WO | WO 2007/036880 A1 | | 4/2007 |

OTHER PUBLICATIONS

Heer et al., "Ultrasound training: the virtual patient", Ultrasound Obstet Gynecol, vol. 24, pp. 440-444, 2004. (Year: 2004).*

Ehricke, "SONOSim3D: a multimedia system for sonography simulation and education with an extensible case database", European Journal of Ultrasound, vol. 7, pp. 225-230, 1998. (Year: 1998).*

Ehricke et al., "SONOSim3D: a multimedia system for sonography simulation and education with an extensible case database", European Journal of Ultrasound, vol. 7, 1998, pp. 225-230.

Heer et al., "Ultrasound training: the virtual patient", Ultrasound Obstet. Gynecol., 2004, vol. 24, pp. 440-444.

International Search Report and Written Opinion for patent application PCT/EP2008/058465, dated Aug. 29, 2008.

International Search Report and Written Opinion for PCT/EP2008/054832, dated Oct. 2, 2008.

* cited by examiner

ULTRASOUND IMAGING SYSTEM AND METHOD FOR PROVIDING ASSISTANCE IN AN ULTRASOUND IMAGING SYSTEM

CROSS REFERENCE TO RELATED APPLICATIONS

This application is a Continuation of application Ser. No. 12/988,730, filed on Nov. 22, 2010, which was filed as PCT International Application No. PCT/EP2008/054832 on Apr. 22, 2008, all of which are hereby expressly incorporated by reference into the present application.

BACKGROUND OF THE INVENTION

The invention relates to an ultrasound imaging system, in particular for the use in medical examinations. It further relates to a method of providing assistance to the user of an ultrasound imaging system, in particular when a medical examination is performed.

State of the Art

In order to make proper use an ultrasound imaging system in the examination of a patient and to take full advantages of its capabilities, a user in general requires a considerable amount of training. From the prior art, systems are known, that provide the user with training videos to be viewed before performing an examination. For example, the S-Series devices and the M-Turbo system available from SonoSite, Inc. Bothell, Wash., USA are delivered with an USB thumb drive, named an "Education Key™", that contain a combination of system operation video tutorials, application-specific video refresher programs with instructions on how to perform certain exams and procedures, and an image reference library for comparison purposes. The tutorials, programs and images can be viewed on the imaging devices when no examination is performed with the device and the device's display is therefore not required for showing the ultrasound image of the examination.

The U.S. Pat. No. 7,263,710 B1, too, describes a medical diagnostic system that provides video training. According to this disclosure, the medical diagnostic system, e.g. an ultrasound system, along with other medical diagnostic systems is connected via a network with a central service facility. On the central service facility, training videos are stored that can be accessed remotely via the network from the medical diagnostic system and displayed on a display monitor of the system. Once the user has finished viewing the video, he can subsequently perform an examination with the medical diagnostic system, which then for that purpose displays a diagnostic image on the display monitor.

Moreover, several methods have been proposed to aid the user during the performance of an ultrasound examination. For example, the U.S. Pat. No. 6,488,629 B1 discloses an ultrasound imaging system and a method for helping the user of the system to find the correct cut-plane when acquiring an ultrasound image. The screen of the ultrasound scanner is divided into two parts, one of which shows the live image currently acquired and the other shows a previously recorded reference image for comparison. The reference image is cycled in a loop and synchronised with the live image based on the patient's ECG signal.

In the international patent application WO 2007/036880 A1, a user interface is disclosed for creating and organizing ultrasound imaging protocols. The ultrasound imaging protocol guides the sonographer through each view of an examination and specifies the types of images and measurements he or she should take during the examination. The user interface displays graphical representations of ultrasound images characteristic for steps of the protocol and allows for manipulation of these graphical representations in order to change the respective protocol step. The revised protocol can then be saved in the system.

From the international patent application WO 2004/058072 A1, a device for real-time location and tracking in ultrasound imaging of anatomical landmarks of the heart is known. According to this disclosure, from the ultrasound signal a set of parameter values is generated that represent the movement of the cardiac structure over time. From these parameters, information about the position of the anatomical landmark is extracted and an indication of the position is overlaid onto the ultrasound image.

In the U.S. Pat. No. 6,656,120 B2, a device for knowledge-based adjustment of the imaging parameters of an ultrasound imaging system is disclosed. Based on a comparison between a patient information database and a reference image database, the imaging settings are automatically adjusted.

Problem to be Solved by the Invention

It is an objective of the present invention to provide an improved ultrasound imaging system, in particular for the use in medical examinations. The invention further aims to provide an improved method of assisting the user of an ultrasound imaging system, in particular when a medical examination is performed.

Solution According to the Invention

According to the invention, the problem is solved by providing an ultrasound imaging system comprising an ultrasound scanner for acquiring a live ultrasound image of a portion of the anatomy of a patient being examined with the ultrasound imaging system, an assistance means for providing at least one primary demonstration video clip, and at least one video display, wherein the video display is functionally connected with the ultrasound scanner and the assistance means in order to present the primary demonstration video clip simultaneously with a live ultrasound image. Also, the problem is solved by method of assisting the user of an ultrasound imaging system, the method comprising the steps of acquiring a live ultrasound image of a portion of the anatomy of a patient being examined, and presenting on a video display the live ultrasound image simultaneously with a primary demonstration video clip.

In the context of the present invention, the expression "examination procedure" does not only encompass purely diagnostic procedures but also therapeutic or surgical procedures that involve ultrasound imaging, e.g. for guidance as may be the case in the performance of a regional anaesthesia. The live ultrasound image is an ultrasound image created from the current ultrasound signal received by the ultrasound scanner during the examination of the patient with the ultrasound imaging system.

A demonstration video clip is an animated sequence of images demonstrating the performance of a step in the examination procedure. The present invention advantageously can instruct the user as to how he should perform a certain step of the procedure while at the same time allowing him or her to implement what he is shown. It is an achievable advantage of the invention that the user requires less experience in the use of the ultrasound system and in the performance of a given procedure to be able perform this procedure and come to a diagnosis. Thus, less training may be required, thereby saving costs.

It is another achievable advantage that the ultrasound imaging system according to the invention can itself be used as a training tool both for introductory training and for continued training. E.g., by means of the system, an experienced user may quickly learn a new procedure or a new diagnosis. Using the system, the user may also rehearse procedures or diagnoses he has already learned. With the help of the present invention, training may be achieved with less or even entirely without the involvement of an instructor, thereby significant reducing training costs. Also, with the present invention the advantage can be achieved that users who have been trained on a different system can easily get acquainted to the system according to the invention.

The system according to the invention may be used by less qualified personnel, thereby expanding the market for medical ultrasound imaging. Thus, the technology can be made available to a greater number of patients, increasing the quality of health care provided to these patients.

It is a further achievable advantage of the invention that even for an experienced user, handling of the system is more intuitive than in conventional systems. He may thus perform a procedure quicker and arrive faster and more confidently to a diagnosis, thereby saving costs and improving quality.

DESCRIPTION OF PREFERRED EMBODIMENTS OF THE INVENTION

Preferred features of the invention which may be applied alone or in combination are discussed in the dependent claims.

A demonstration video clip, such as the primary demonstration video clip and the secondary demonstration video clip discussed further below, preferably shows the position, orientation, and motion of a probe of the ultrasound scanner relatively to the patient's anatomy in the respective step of the examination procedure. The demonstration video clip may for example be a recording of an examination that has been performed on a real subject or a phantom. Alternatively, it may be the recording of a simulation using an anatomic model. The demonstration video clip may also be generated in real-time inside or outside the ultrasound imaging system, preferably by the assistance means. If the clip is be pre-recorded, it may be stored in a memory, e.g. inside the ultrasound imaging system, on a separate memory device such as SonoSite's Education Key™, or on a remote service facility such as the one disclosed in U.S. Pat. No. 7,263,710 B1. The corresponding disclosure of the latter publication is incorporated into the present application by reference.

In a preferred embodiment of the invention, the assistance means can in addition to the at least one primary demonstration video clip provide at least one ultrasound image video clip, which corresponds to one of the at least one primary demonstration video clips. The demonstration video clip corresponds to the ultrasound image video clip in that the ultrasound image video clip represents the animated ultrasound image that results or would result from performing the procedural step as demonstrated in the demonstration video clip. Moreover, preferably the video display is functionally connected with the assistance means in order to present the ultrasound image video clip simultaneously with the primary demonstration video clip and the live ultrasound image. Thus, the ultrasound image video clip which corresponds to the primary demonstration video clip is presented simultaneously with the live ultrasound image and the primary demonstration video clip.

The inventors have found that, advantageously, the demonstration of a procedural step simultaneously with presenting the corresponding ultrasound image allows the user to more naturally grasp the relationship between the manipulation of the scanning probe and the ultrasound image. Hence, this embodiment of the invention can help the user to reproduce the procedural steps and interpret the live ultrasound image. It is believed, without prejudice, that this is at least partly due to the fact that the user can on one hand compare the live ultrasound image with the ultrasound image video clip, and on the other hand his own handling of the ultrasound probe (which result in the live ultrasound image) with the demonstration of the procedural step in the primary demonstration video clip (which corresponds to the ultrasound image video clip).

Similar to the demonstration video clip, the ultrasound image video clip may be the ultrasound image that has been obtained in the examination of a real subject or a phantom or it may be the result of a simulation based on an anatomic model.

In a preferred embodiment on the invention, the assistance means comprises a synchroniser for synchronising the presentation of the ultrasound image video clip with the presentation of the demonstration video clip, so that the primary demonstration video clip runs in synchrony with the ultrasound image video clip. Synchrony between a demonstration video clip and the ultrasound image video clip means that at any moment the ultrasound image video clip shows the ultrasound image that results or would result from the position and orientation of the ultrasound scanning probe in the demonstration video clip at the respective moment. Thus, as the probe moves in the demonstration video clip, the ultrasound image in the ultrasound image video clip changes correspondingly. Moreover, preferably if in the demonstration video clip the patient is moved or manipulated in a way that would have an effect on the ultrasound image obtained from the patient, the ultrasound image in the ultrasound image video clip changes correspondingly.

The synchronised presentation of the performance of the procedural step and the corresponding ultrasound image can make it even easier for the user to understand the relationship between his manipulation of the scanning probe and the resulting ultrasound image. The user can e.g. see what motion helps in a particular procedural step to proceed from a landmark to a target feature or to identify a certain anatomic structure. As to the identification of anatomic structures, it can e.g. be demonstrated that nerves can be distinguished from bones by the fact that the nerve ultrasound image is stronger at some incident angles than others, while the image of bones is the same at all angles. Proper manipulation of the probe and interpretation of the ultrasound image can thus be facilitated.

If the demonstration video clip and the ultrasound image video clip are pre-recorded, synchronisation will preferably involve ensuring that the presentation of these video clips starts synchronously on the video display. It may also involve adjusting the speed in which one or both of the video clips are presented.

In a preferred embodiment of the invention, in addition to the primary demonstration video clip the assistance means can provide at least one secondary demonstration video clip, which corresponds to one of the at least one primary demonstration video clips. Preferably, the video display is functionally connected with the assistance means in order to present the secondary demonstration video clip simultaneously with the primary demonstration video clip, the live ultrasound image, and, preferably, the ultrasound image video clip. Thus, in addition to the primary demonstration video clip a corresponding secondary demonstration video clip is shown on the video display. Preferably, the primary demonstration video clip and the corresponding secondary demonstration video clip show different views of the same step of the examination. This embodiment of the invention can improve the comprehensibility of the demonstration of the procedural step and can make it easier for the user to understand the relationship between the motion of the probe and the resulting ultrasound image as shown in the ultrasound image video dip.

In a preferred embodiment of the invention, one demonstration video clip shows the step of the examination procedure in a perspective view. Preferably one demonstration video clip shows the step of the examination procedure in a cross-sectional view. More preferably, one of the first and the second demonstration video clips shows the perspective view while the other shows the cross-sectional view. The perspective view can be semi-transparent so that the user does not only see the patient's skin but also the underlying tissue, including bones, blood vessels, nerves and other organs. In the cross-sectional view, preferably the cross-sectional plane essentially coincides with the scanning plane of the ultrasound image video clip. Hence, if the scanning plane changes over the course of the ultrasound image video clip, so does the cross-sectional plane of the cross-sectional view. Due to the provision of both a perspective view and a cross-sectional view together with the ultrasound image video clip, the user can more easily move his or her anatomical perception from the 3-dimensional space in which the probe is manipulated to the 2-dimensional imaging slice.

Preferably, the synchroniser synchronises the presentation of the secondary demonstration video clip with the presentations of the primary demonstration video clip and, preferably, the ultrasound image video clip. In other words, the secondary demonstration video clip runs in synchrony with the primary demonstration video clip and the ultrasound image video clip. This can further help the user to understand the relationship between the motion of the probe and the resulting ultrasound image as shown in the ultrasound image video clip.

In a preferred embodiment of the invention, in the primary and/or the secondary demonstration video clip, there is the imaging slice indicated, from which the ultrasound image of the corresponding ultrasound image video clip results or would result. This can assist the user in interpreting the ultrasound image video clip. The imaging slice may for example be illustrated in the form of a quadrangular frame or a shaded area adjacent to the representation of the probe.

To complement the graphical information provided to the user with written information, in a preferred embodiment of the invention text is displayed on the video display, e.g. in one or more text fields. The text may e.g. explain in more detail how to handle the probe of the ultrasound scanner or how to interpret the ultrasound image and derive a diagnosis. The text field(s) may be adjacent to one or more of the locations on the video display where the demonstration video clips or the ultrasound image video clips are presented.

In ultrasonography, the properties of the image in general and its quality in particular are a function of the scanner's imaging settings. Finding the right imaging settings may be essential for a user to perform the procedure properly and arrive at the correct diagnosis. In a preferred embodiment of the invention, the scanner's imaging settings are adjusted by providing the scanner with a set of image parameters. The set of image parameters preferably includes at least one of a group of parameters comprising imaging depth, number of focal zones, and imaging mode. Examples for imaging modes are B-mode, C-mode, M-mode, PW-Doppler-mode and CW-Doppler-mode.

Preferably, the assistance means can provide at least one set of image parameter values corresponding to at least one of the demonstration video clips and/or ultrasound image video clips. More preferably, the assistance means is functionally connected with the ultrasound scanner to adjust the ultrasound scanner's imaging settings according to the set of image parameter values that corresponds to the demonstration video clip and/or ultrasound image video clip to be presented on the video display. This embodiment of the invention can help users who are inexperienced or unfamiliar with the image parameters and the effect on the image quality to obtain a good image. Moreover, by reducing the amount of image manipulation which the user has to perform, it allows users to concentrate on performing the procedure and obtaining the diagnosis rather than dealing with the technical details of the image generation. Advantageously, the user may thus save valuable time that he or she would otherwise require to adjust the settings of the ultrasound scanner. Moreover, this embodiment of the invention may help to avoid sub-optimal images that are obtained because in order to save time the user leaves the parameters at some typical values all the time. Preferably, the set of image parameter values that corresponds to the ultrasound image video clip is chosen so that the live ultrasound image obtained is similar to the image shown in the ultrasound image video clip. In other words, the image parameters are essentially those that result or would result into the image shown in the ultrasound image video clip.

In a preferred embodiment of the invention, the assistant means can provide at least one procedure demonstration set comprising several primary demonstration video clips, each demonstrating a different step in the examination procedure. Preferably, the assistant means is functionally connected with the video display to provide the primary demonstration video clips for presentation on the video display. Moreover, the procedure demonstration set preferably comprises several ultrasound image video clips, each clip corresponding to a different one of the primary demonstration video clips, and the assistant means is functionally connected with the video display in order to present the ultrasound image video clips simultaneously with the primary demonstration video clips in the same order. Preferably, the synchroniser can synchronise the presentation of each ultrasound image video clip with the presentation of its corresponding primary demonstration video clip.

A preferred procedure demonstration set comprises several secondary demonstration video clips, each corresponding to a different one of the primary demonstration video clips, and the assistant means is functionally connected with the video display in order to present the secondary demonstration video clips simultaneously with the primary demonstration video clips in the same order. Preferably, the synchroniser can synchronise the presentation of each secondary presentation video clip with the presentation of its corresponding primary demonstration video clip.

The present invention also encompasses embodiments of the invention which differ from the above embodiments contemplating procedure demonstration sets of several video clips in that some of the primary demonstration video clips are replaced by demonstration still images. Similarly, some or all of the corresponding ultrasound video clips and/or the secondary demonstration video clips may be replaced by ultrasound still images or demonstration still images, respectively. These alternative embodiments of the invention recognize the fact that some of the procedural steps may not involve motions relevant to the demonstration of the procedural step and may therefore be represented by still images. These embodiments of the invention may advantageously save storage and computing resources. Preferably, if a primary demonstration video clip is replaced by a still image, the corresponding ultrasound image video clip, if any, is replaced by a corresponding still image and the corresponding secondary demonstration video clip, if any, is equally replaced by a still image.

The preferred procedure demonstration set will comprise one primary demonstration video clip or still image for each step of the examination procedure. A procedure generally comprises at least the steps of (1) positioning the patient and finding a first landmark detectable with the ultrasound scanner, and (2) navigating with the scanner's probe from the landmark to the target. Further steps may e.g. include (3) studying the target and (4) inserting a needle. Preferably, the primary demonstration video clip or still image presented on the video screen changes, in an appropriate moment, to another primary demonstration video clip or still image in which the performance of another step in the examination procedure is demonstrated. Correspondingly, the ultrasound image video clip or still image preferably changes to another ultrasound image video clip or still image which corresponds to the other primary demonstration video clip or still image and/or the secondary demonstration video clip or still image changes to another secondary demonstration video clip or still image which corresponds to the other primary demonstration video clip or still image. Preferably, the primary demonstration video clip changes synchronously with the ultrasound image video clip and/or the secondary demonstration video clip.

In general, if the user of the ultrasound imaging system does not intervene, the demonstration video of the current procedural step and the corresponding ultrasound image video are shown continuously in a loop. In a preferred embodiment, the ultrasound imaging system comprises a step control that is functionally connected with the assistant means in order upon operation of the step control by the user of the ultrasound system to provide another primary demonstration video or still image (and, if any, the corresponding ultrasound video clip or still image and/or secondary demonstration video clip or still image) for presentation on the video display. The step control may e.g. comprise several virtual buttons on the video display that the user can operate to choose the step he wishes to view next. Thus, e.g., the primary demonstration video clip presented on the video screen may change to a subsequent primary demonstration video clip or still image in which the performance of a subsequent, preferably the next, step in the examination procedure is demonstrated. Preferably, upon operation of the step control by the user, the assistant means also provides the ultrasound image video clip or still image and/or the secondary demonstration video corresponding to the respective primary demonstration video clip or still image. Hence, advantageously, by means of the step control, the user can go sequentially through all steps of the procedure.

In a preferred embodiment of the invention, the assistance means can provide several procedure demonstration sets, each set demonstrating steps of a different examination procedure. Preferably, the ultrasound imaging system comprises a procedure control that is functionally connected with the assistant means in order upon operation of the procedure control by the user of the ultrasound imaging system to select from the several procedure demonstration sets the set to be provided for presentation on the video display. Thus, advantageously, the user can select one of several procedures and then go through the steps of the procedure as described above.

The components of the ultrasound imaging system according to the invention, in particular the assistance means, the video display, the ultrasound scanner, the memory, the step control, and the procedure control, can be implemented by hardware, by software, or by a combination of both. Accordingly, in the context of the present invention a functional connection between components of the ultrasound imaging system preferably is a communication between these components, involving an exchange of data, either in one direction or in both directions. In the case of software, such communication may simply involve the exchange of one or more parameter values from one software component, e.g. a software component which controls a processing unit to implement the step control, to another software component, e.g. a software component that controls the same processing unit to implement the assistance means. It may, however, also involve the exchange of one or more electric, magnetic, microwave, or optical signals from one hardware component, e.g. the hardware component which is controlled by the assistance means-software, to another hardware component, e.g. a video display-hardware.

BRIEF DESCRIPTION OF THE DRAWINGS

The invention is illustrated in greater details with the aid of schematic drawings.

DETAILED DESCRIPTION OF AN EMBODIMENT OF THE INVENTION

Figure 1:
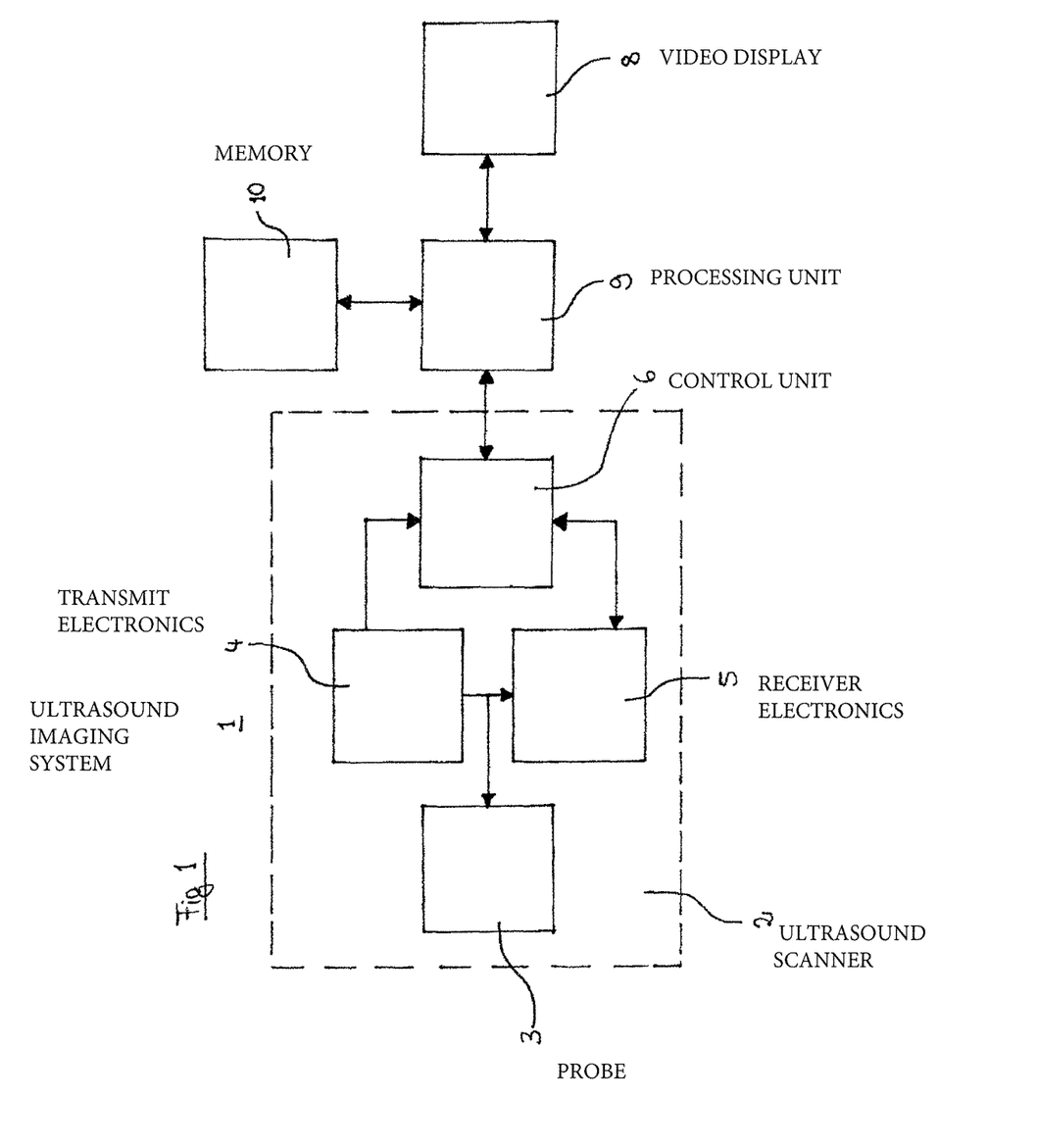
FIG. 1 shows a block diagram of an ultrasound imaging system according to the present invention.

An embodiment of the ultrasound imaging system 1 according to the invention is illustrated in FIG. 1 by means of a simplified block diagram. The system comprises an ultrasound scanner 2 with a probe 3, transmit electronics 4, receive electronics 5, and a control unit 6. A user of the ultrasound imaging system 1 can bring the probe 3 into contact with a patient in order to obtain a live ultrasound image 7 of an imaging slice defined by the position and orientation of the probe 3. The probe 3 contains transducers for generating ultrasound signals and receiving reflections of these ultrasound signals from the body of the patient. For example, the transducers for ultrasound generation and reception can be provided by an array of piezo elements. Alternatively, opto-electrical ultrasound sensors may be used for the reception of the reflected ultrasound signals. The probe 3 is connected via a flexible cable with the rest of the ultrasound system 1 so that it can be easily manipulated by the user during the examination.

The transmit electronics 4 comprise multiple channels that are connected directly or via one or more multiplexers to the ultrasound generating elements of the probe 3, for example piezo elements. Electric pulses are generated in each individual channel, and the relative timing of the pulses can be varied accurately enough to perform a transmit focusing in the lateral direction at different depths. The transmit electronics are implemented as a mixed signal electronics board or an ASIC, and include high voltage pulsers for generating the electric pulses.

The electric signals generated by the receiving piezo elements or opto-electrical ultrasound sensors in response to the reflected ultrasound signals are processed by the receive electronics 5. Processing includes the amplification of the analogue signals coming from the receiving transducers and the conversion into digital signals. The receive electronics 5 comprise a mixed signal electronics board or ASIC, which includes amplifiers and analogue-to-digital converters.

Both, the transmit electronics 4 and the receive electronics 5 are controlled by the ultrasound scanner's 2 control unit 6. The control unit's 6 tasks includes beam-forming and the processing of the digital signals received from the receive electronics 5. For this purpose, the control unit 6 comprises a digital signal processor (DSP), e.g. in the form of a field programmable gate array (FPGA).

The ultrasound imaging system 1 further comprises a video display 8 which is in communication with the scanner's 2 control unit 6 via a processing unit 9 in order to present a life ultrasound image 7 based on the ultrasound signals received by the probe 3. In the present example, the processing unit 9 comprises a CPU and GPU and performs its tasks at least partially by means of a software program. It performs scan-conversion and image processing functions to prepare the signals coming from the control unit 6 for presentation on the video display 8. In addition, the assistance means in the present example is software-implemented in the processing unit 9 so that, amongst other things, the processing unit 9 provides primary and secondary demonstration videos clips or still images and ultrasound image videos or still images for presentation on the video display 8. For this purpose, the videos and still images are stored in a memory 10 in an appropriate directory structure, so that they can easily be retrieved by the processing unit 9 for presentation on the video display 8. Moreover, parameter values corresponding to the ultrasound image video clips are stored in the memory and retrieved by the processing unit 9 for adjusting the settings of the ultrasound scanner 6. A suitable memory 10 is a flash memory drive. In the memories directory structure, each procedure has a different directory containing the required video or image files of all steps in this procedure.

Figure 2:
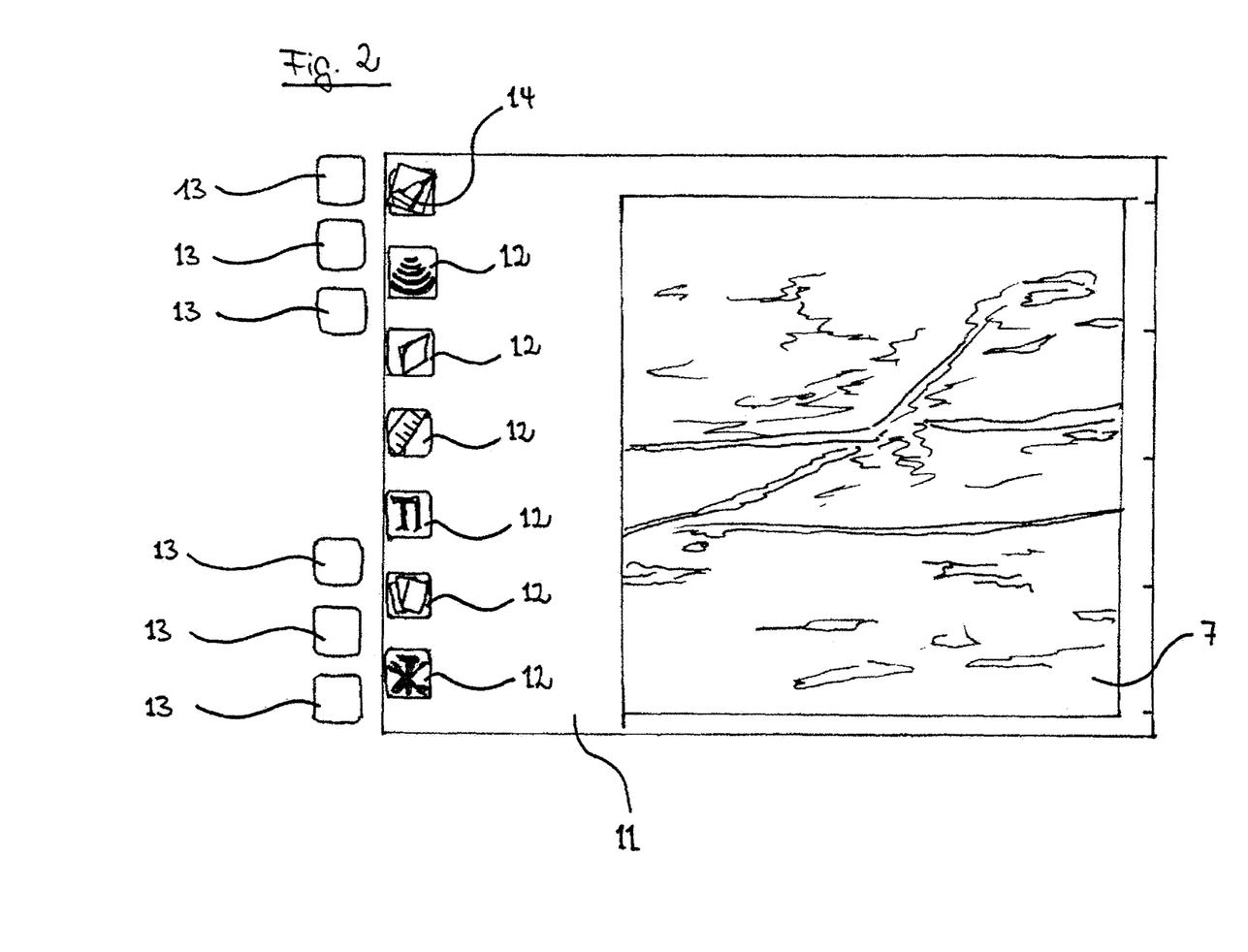
FIG. 2 shows a screen of a user interface presented on the video display of an ultrasound imaging system according to the invention, the screen comprising several controls and a live ultrasound image.
Figure 3:
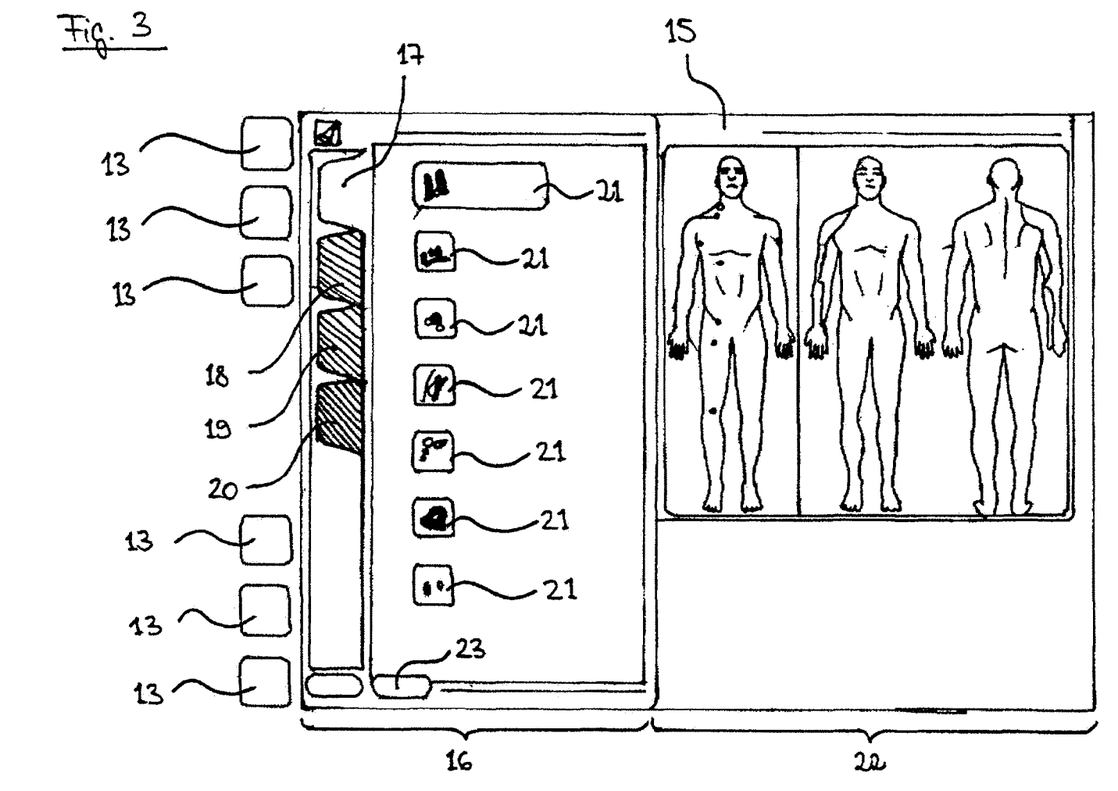
FIG. 3 shows another screen of the user interface presented on the video display, which screen comprises a procedure control.
Figure 4:
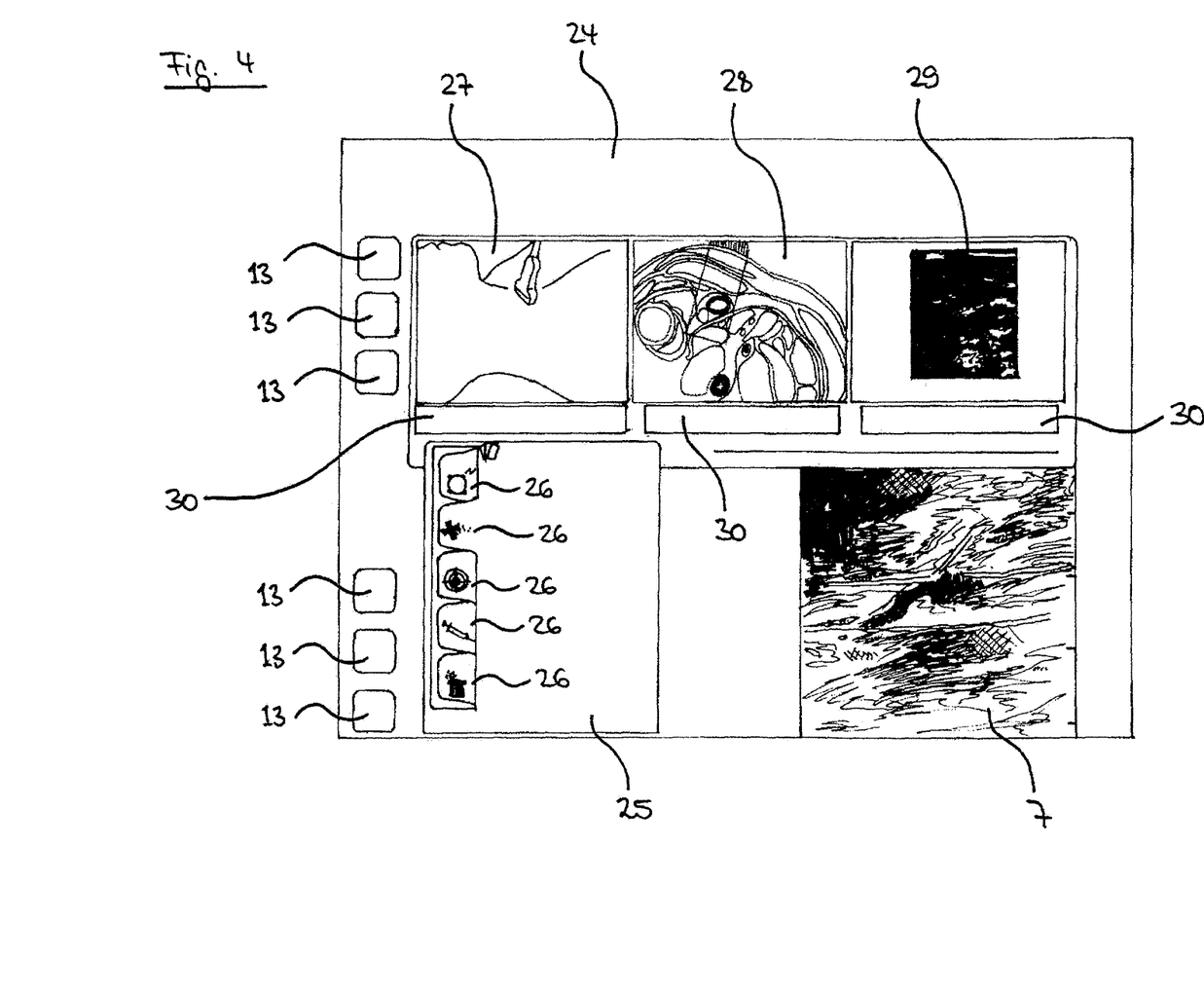
FIG. 4 shows yet another screen of the user interface presented on the video display, which screen comprises a step control and presentations of the first demonstration video clip, the second demonstration video clip, the ultrasound image video clip and the ultrasound life image.

The processing unit 9 generates on the video display 8 a user interface comprising multiple screens, three of which are shown in FIGS. 2 to 4. The screens comprise software-implemented controls and serve to present the live ultrasound image along with video clips, still images, and written information. FIG. 2 shows a first screen 11 of the user interface which comprises the life ultrasound image 7 on the right hand side and various controls 12, 13, 14 on the left hand side. The controls can be operated via appropriate input means, e.g. a computer mouse or touch screen sensors on the video display 8. With the controls 12, 13, the user can, adjust various settings of the ultrasound imaging system 1, make measurements and annotations and administer patient records. Moreover, there is a procedure control 14 in the top left corner, which leads the user to the procedure selection screen 15 shown in FIG. 3 which replaces the screen of FIG. 2.

On the procedure selection screen 15, the user finds in an area on the left hand side a procedure control 16 comprising a number of virtual tabs 17, 18, 19, 20 and buttons 21 representing different procedures. The uppermost tab 17, for example, produces a list of buttons 21 for procedures regarding the field of regional anaesthesia, while the tab 18 below produces a list of procedure buttons 21 regarding vascular access. There is also a tab 20 which produces a list of "favourite" procedure buttons 21, which list the user can customize to include the procedures that he or she uses most often. By operating one of the procedure buttons 21, the user can choose the corresponding procedures and, on the right hand side 22 of the screen, obtains some general information regarding the procedure, generally in the form of still images. Pressing a cue card button 23 on the bottom of the screen 15 leads the user to a cue card screen 24 corresponding to the selected procedure. The cue card screen 24 replaces the procedure selection screen 15 of FIG. 3.

On the cue card screen 24 shown in FIG. 4, on the bottom left hand side a step control 25 is shown which comprises several virtual tabs 26 representing the steps of the procedure and arranged from top to bottom in the order in which they have to be performed. The user can select the step he seeks to perform next by operating the corresponding tab 26 of the step control 25. As a result, on top of the cue card screen 24, the primary demonstration video clip 27 or still image, the secondary demonstration video clip 28 or still image and the ultrasound image video clip 29 or still image, all retrieved by the processing unit 9 from the memory 10, are shown in that order from left to right. In the bottom right corner of the cue card screen 24, the life video image 7 is shown. If the three images 27, 28, 29 in the upper row are video clips, they are synchronised by means of a synchroniser software-implemented in the processing unit 9, so that a movement of the probe 3 shown in the primary demonstration video clip 27 corresponds to a movement of the probe 3 in the secondary demonstration video clip 28 and the representation of the ultrasound image of this slice in the ultrasound image video clip 29.

More particularly, in the example of FIG. 4, there is a primary demonstration video clip 27 that shows the movement of the probe 3, e.g. from a landmark to a target, in a perspective view based on an anatomic model of a human, a secondary demonstration video clip 28 that shows the movement in a cross-sectional view based on the same anatomic model, and an ultrasound image video clip 29 that shows the ultrasound image that would result from the procedure. The body of the patient in the perspective view is semi-transparent (not shown in the Figure), so that the spinal cord, the mayor blood vessels and the thyroid gland are visible. Both, in the perspective view of the first demonstration video clip 27 and the cross-sectional view of the second demonstration video clip 28, a shaded quadrangle indicates the imaging slice that would corresponds to the ultrasound image shown in the ultrasound image video clip 29. Below the areas on the screen where the video clips or still images are shown, text boxes are 30 providing additional information.

Moreover, the image parameter values corresponding to the ultrasound image video clips 29 are retrieved by the processing unit 9 from the memory 10. The processing unit 9 sends these parameters to the ultrasound scanner 2 to adjust the ultrasound scanner's 2 imaging settings to those suitable for the current procedural step.

Using the perspective view, the cross-sectional view and the corresponding ultrasound image of the demonstration, the user's anatomic perception is guided from tree dimensions to two dimensions and from there to the ultrasound image. By comparison of the demonstration with his own handling of the probe 3 and the live ultrasound image 7, the user can easily reproduce the demonstrated step of the procedure and interpret the live image he obtains.

The features described in the above description, claims and figures can be relevant to the invention in any combination.

The invention claimed is:

1. An ultrasound imaging system comprising:
    an ultrasound scanner including a probe configured to acquire a live ultrasound image of a patient being examined;
    a display; and
    a processor configured to:
        control the display to display a pre-recorded primary demonstration video presenting a plurality of pre-recorded video clips respectively corresponding to surgical procedure steps in a surgical procedure to be performed on the patient being examined, wherein the pre-recorded video clips display a change in a position, orientation and motion of an animated probe moving from a landmark to a target relative to an anatomy of a human body occurring in the surgical procedure steps and wherein the surgical procedure steps include a step of moving a surgical instrument into the patient,
        control the display to display pre-recorded ultrasound images corresponding to the change in the position, orientation and motion of the animated probe relative to the anatomy of the human body occurring in the surgical procedure steps, wherein the pre-recorded ultrasound images are displayed simultaneously and synchronously with the corresponding pre-recorded video clips,
        control the display to display the live ultrasound image of the patient being examined as a user using the probe follows the change in the position, orientation and motion of the animated probe in the surgical procedure steps presented in the pre-recorded video clips,
        display a plurality of virtual tabs representing the surgical procedure steps to be performed on the patient being examined, and
        in response to selection of a first virtual tab among the plurality of virtual tabs, control the display to display a first pre-recorded video clip representing a first step of the surgical procedure steps to be performed on the patient being examined and to display a first pre-recorded ultrasound image corresponding to the change in the position, orientation and motion of the animated probe in the first pre-recorded video clip.

2. The ultrasound imaging system according to claim 1, further comprising:
    a memory configured to store the pre-recorded video clips and the pre-recorded ultrasound images.

3. The ultrasound imaging system according to claim 1, wherein the processor is further configured to:
    in response to selection of a second virtual tab among the plurality of virtual tabs, control the display to display a second pre-recorded video clip representing a second step of the surgical procedure steps to be performed on the patient being examined and to display a second pre-recorded ultrasound image corresponding to the change in the position, orientation and motion of the animated probe in the second pre-recorded video clip.

4. The ultrasound imaging system according to claim 3, wherein the second step is a step immediately following the first step in the surgical procedure being performed on the patient.

5. The ultrasound imaging system according to claim 3, wherein the processor is further configured to:
    control the display to sequentially display the plurality of virtual tabs on a portion of the display to indicate an order of the surgical procedure steps the user should follow in the surgical procedure.

6. The ultrasound imaging system according to claim 1, wherein the processor is further configured to:
    control the display to display a pre-recorded secondary demonstration video presenting a plurality of pre-recorded images respectively corresponding to the surgical procedure steps in the surgical procedure to be performed on the patient being examined,
    wherein the plurality of pre-recorded images correspond to cross-sectional images of the anatomy of the human body as the position, orientation and motion of the animated probe moves from the landmark to the target relative to the anatomy of the human body, and
    wherein the plurality of pre-recorded images are displayed simultaneously and synchronously with the corresponding pre-recorded video clips in the pre-recorded primary demonstration video and the pre-recorded ultrasound images in the pre-recorded secondary demonstration video and with the live ultrasound image.

7. The ultrasound imaging system according to claim 1, wherein the processor is further configured to:
    retrieve image parameter values corresponding to a current step and send the image parameter values to adjust imaging settings of the ultrasound scanner.

8. The ultrasound imaging system according to claim 1, wherein the processor is further configured to:
    control the display to display text fields explaining how to handle the probe of the ultrasound scanner or how to interpret the ultrasound image and derive a diagnosis.

9. The ultrasound imaging system according to claim 1, wherein the step of moving a surgical instrument into the patient comprises inserting a needle.

10. A method of instructing a user on how to use an ultrasound imaging system having an ultrasound scanner with a probe configured to acquire a live ultrasound image of a patient being examined, the method comprising:
    displaying, on a display included in the ultrasound imaging system, a pre-recorded primary demonstration video presenting a plurality of pre-recorded video clips respectively corresponding to surgical procedure steps in a surgical procedure to be performed on the patient being examined, wherein the pre-recorded video clips display a change in a position, orientation and motion of an animated probe moving from a landmark to a target relative to an anatomy of a human body occurring in the surgical procedure steps and wherein the surgical procedure steps include a step of moving a surgical instrument into the patient;
    displaying, via the display, pre-recorded ultrasound images corresponding to the change in the position, orientation and motion of the animated probe relative to the anatomy of the human body occurring in the surgical procedure steps, wherein the pre-recorded ultrasound images are displayed simultaneously and synchronously with the corresponding pre-recorded video clips;
    displaying, via the display, the live ultrasound image of the patient being examined as the user using the probe follows the change in the position, orientation and motion of the animated probe in the surgical procedure steps presented in the pre-recorded video clips;

displaying a plurality of virtual tabs on the display representing the surgical procedure steps to be performed on the patient being examined; and in response to selection of a first virtual tab among the plurality of virtual tabs, displaying a first pre-recorded video clip on the display representing a first step of the surgical procedure steps to be performed on the patient being examined and displaying on the display a first pre-recorded ultrasound image corresponding to the change in the position, orientation and motion of the animated probe in the first pre-recorded video clip.

11. The method according to claim 10, further comprising:

storing the pre-recorded video clips and the pre-recorded ultrasound images in a memory associated with the ultrasound system.

12. The method according to claim 10, further comprising:

in response to selection of a second virtual tab amount the plurality of virtual tabs, displaying on the display a second pre-recorded video clip representing a second step of the surgical procedure steps to be performed on the patient being examined and displaying on the display a second pre-recorded ultrasound image corresponding to the change in the position, orientation and motion of the animated probe in the second pre-recorded video clip.

13. The method according to claim 12, wherein the second surgical procedure step is a step immediately following the first step in the surgical procedure being performed on the patient.

14. The method according to claim 10, further comprising:

sequentially displaying the plurality of virtual tabs on a portion of the display to indicate an order of the surgical procedure steps the user should follow in the surgical procedure.

15. The method according to claim 10, further comprising:

displaying, via the display, a pre-recorded secondary demonstration video presenting a plurality of pre-recorded images respectively corresponding to the surgical procedure steps in the surgical procedure to be performed on the patient being examined, wherein the plurality of pre-recorded images correspond to cross-sectional images of the anatomy of the human body as the position, orientation and motion of the animated probe moves from the landmark to the target relative to the anatomy of the human body, and wherein the pre-recorded ultrasound images are displayed simultaneously and synchronously with the corresponding pre-recorded video clips in the pre-recorded primary demonstration video and the pre-recorded images in the pre-recorded secondary demonstration video and with the live ultrasound image.

16. The method according to claim 10, further comprising:

retrieving image parameter values corresponding to a current step and send the image parameter values to adjust imaging settings of the ultrasound scanner.

17. The method according to claim 10, further comprising:

displaying text fields fields explaining how to handle the probe of the ultrasound scanner or how to interpret the ultrasound image and derive a diagnosis.

18. The method according to claim 10, wherein the step of moving a surgical instrument into the patient comprises inserting a needle.

* * * * *